(12) United States Patent
Gueniche

(10) Patent No.: US 8,481,299 B2
(45) Date of Patent: Jul. 9, 2013

(54) USE OF PROBIOTIC MICROORGANISMS TO LIMIT SKIN IRRITATION

(75) Inventor: Audrey Gueniche, Rueil Malmaison (FR)

(73) Assignees: L'Oreal, Paris (FR); Nestec S.A, Vevey (CH)

( * ) Notice: Subject to any disclaimer, the term of this patent is extended or adjusted under 35 U.S.C. 154(b) by 170 days.

(21) Appl. No.: 12/717,438

(22) Filed: Mar. 4, 2010

(65) Prior Publication Data

US 2010/0226892 A1 Sep. 9, 2010

Related U.S. Application Data

(60) Provisional application No. 61/202,627, filed on Mar. 19, 2009.

(30) Foreign Application Priority Data

Mar. 4, 2009 (FR) ..................................... 09 51362

(51) Int. Cl.
*C12N 1/20* (2006.01)

(52) U.S. Cl.
USPC ...................... 435/252.9; 424/93.45; 424/93.7

(58) Field of Classification Search
None
See application file for complete search history.

(56) References Cited

U.S. PATENT DOCUMENTS

| | | | |
|---|---|---|---|
| 3,156,355 A | 11/1964 | Rodgers | |
| 4,464,362 A | 8/1984 | Kludas et al. | |
| 4,717,720 A | 1/1988 | Shroot et al. | |
| 4,740,519 A | 4/1988 | Shroot et al. | |
| 4,925,658 A | 5/1990 | Shroot et al. | |
| 5,110,593 A * | 5/1992 | Benford | 424/401 |
| 5,326,565 A | 7/1994 | Critchley et al. | |
| 5,602,183 A * | 2/1997 | Martin et al. | 514/724 |
| 5,614,209 A | 3/1997 | Ford | |
| 5,656,268 A | 8/1997 | Sorodsky | |
| 5,756,088 A | 5/1998 | Matsuura et al. | |
| 5,851,556 A | 12/1998 | Breton et al. | |
| 5,882,665 A | 3/1999 | Meyers et al. | |
| 6,139,850 A | 10/2000 | Hahn et al. | |
| 6,156,355 A | 12/2000 | Shields, Jr. et al. | |
| 6,254,886 B1 | 7/2001 | Fusca et al. | |
| 6,287,553 B1 | 9/2001 | Alaluf et al. | |
| 6,329,002 B1 | 12/2001 | Kim et al. | |
| 6,423,325 B1 | 7/2002 | Alaluf et al. | |
| 6,461,627 B1 | 10/2002 | Ichioka et al. | |
| 6,506,413 B1 | 1/2003 | Ramaekers | |
| 6,905,692 B2 | 6/2005 | Farmer | |
| 7,179,460 B2 | 2/2007 | Dennin et al. | |
| 7,547,527 B2 | 6/2009 | Baur et al. | |
| 7,651,680 B2 | 1/2010 | Breton et al. | |
| 8,101,167 B2 | 1/2012 | Gueniche | |
| 2002/0187167 A1 | 12/2002 | Vacher et al. | |
| 2003/0003107 A1 | 1/2003 | Farmer | |
| 2003/0039672 A1 | 2/2003 | Ginger et al. | |
| 2003/0049231 A1 | 3/2003 | Baur et al. | |
| 2004/0001817 A1 | 1/2004 | Giampapa | |
| 2004/0013706 A1 * | 1/2004 | Baur et al. | 424/439 |
| 2004/0029829 A1 | 2/2004 | Miyazaki et al. | |
| 2004/0110270 A1 | 6/2004 | Dennin et al. | |
| 2005/0106131 A1 | 5/2005 | Breton et al. | |
| 2005/0180961 A1 | 8/2005 | Pecquet et al. | |
| 2006/0002910 A1 | 1/2006 | Baur et al. | |
| 2006/0008453 A1 | 1/2006 | Breton et al. | |
| 2006/0018986 A1 | 1/2006 | Breton | |
| 2006/0099196 A1 | 5/2006 | Breton et al. | |
| 2006/0171936 A1 | 8/2006 | Gueniche et al. | |
| 2007/0129428 A1 | 6/2007 | Richelle et al. | |
| 2008/0206171 A1 | 8/2008 | Gueniche | |
| 2009/0232785 A1 | 9/2009 | Breton et al. | |
| 2010/0272839 A1 | 10/2010 | Gueniche et al. | |
| 2010/0278793 A1 | 11/2010 | Gueniche et al. | |
| 2011/0014248 A1 | 1/2011 | Castiel et al. | |

FOREIGN PATENT DOCUMENTS

| | | |
|---|---|---|
| DE | 198 30 528 A1 | 7/1999 |
| DE | 198 06 890 A1 | 8/1999 |
| DE | 202 02 562 U1 | 6/2002 |
| EP | 0 043 128 A1 | 1/1982 |
| EP | 0 110 550 A1 | 6/1984 |
| EP | 0 199 636 A1 | 10/1986 |
| EP | 0 319 028 A1 | 6/1989 |
| EP | 0 325 540 A1 | 7/1989 |
| EP | 0 399 909 A1 | 11/1990 |
| EP | 0 402 072 A2 | 12/1990 |
| EP | 0 737 471 A2 | 10/1996 |
| EP | 0 774 249 A2 | 5/1997 |
| EP | 0 806 933 B1 | 11/1997 |
| EP | 0 825 196 A2 | 2/1998 |
| EP | 0 852 949 A2 | 7/1998 |
| EP | 0 904 784 A1 | 3/1999 |
| EP | 0 919 226 A2 | 6/1999 |
| EP | 0 919 266 A2 | 6/1999 |
| EP | 0 931 543 A1 | 7/1999 |
| EP | 0 945 126 A2 | 9/1999 |
| EP | 1 110 555 A1 | 6/2001 |
| EP | 1 169 925 A1 | 1/2002 |
| EP | 1 236 463 A1 | 9/2002 |
| EP | 1 344 528 A1 | 9/2003 |
| EP | 1 364 586 A1 | 11/2003 |
| EP | 1 374 913 A1 | 1/2004 |

(Continued)

OTHER PUBLICATIONS

Saavedra et al., Am J Clinical Nutrition, 2001;73 (suppl): 1147S-51S.*

(Continued)

*Primary Examiner* — Allison Ford
*Assistant Examiner* — Yvonne Pyla
(74) *Attorney, Agent, or Firm* — Oliff & Berridge, PLC

(57) ABSTRACT

Disclosed are methods directed to the cosmetic use of an effective amount of at least one probiotic microorganism especially from the genus *Lactobacillus* sp. and/or *Bifidobacterium* sp., of a fraction thereof and/or of a metabolite thereof, as an active agent for limiting, preventing or treating skin irritation and/or irritative skin disorders.

10 Claims, 1 Drawing Sheet

FOREIGN PATENT DOCUMENTS

| | | |
|---|---|---|
| EP | 1 593 382 A1 | 11/2005 |
| EP | 1 609 463 A1 | 12/2005 |
| EP | 1 642 570 A1 | 4/2006 |
| EP | 1 731 137 A1 | 12/2006 |
| EP | 2 050 434 A1 | 4/2009 |
| FR | 2 570 377 A1 | 3/1986 |
| FR | 2 738 485 A1 | 3/1997 |
| FR | 2 781 669 A1 | 2/2000 |
| FR | 2 802 088 A1 | 6/2001 |
| FR | 2 811 224 A1 | 1/2002 |
| FR | 2 848 448 A1 | 6/2004 |
| FR | 2 851 889 A1 | 9/2004 |
| FR | 2 872 047 A1 | 12/2005 |
| FR | 2 876 029 A1 | 4/2006 |
| FR | 2 877 222 A1 | 5/2006 |
| FR | 2 889 057 A1 | 2/2007 |
| FR | 2 905 856 A1 | 3/2008 |
| FR | 2 912 917 A1 | 8/2008 |
| KR | 2000039570 A | 7/2000 |
| KR | 2001107152 A | 8/2000 |
| RU | 2 228 184 C2 | 5/2004 |
| WO | WO 96/19184 | 6/1996 |
| WO | WO 99/49877 A2 | 10/1999 |
| WO | WO 00/49885 A1 | 8/2000 |
| WO | WO 00/70972 A1 | 11/2000 |
| WO | WO 01 13927 A2 | 3/2001 |
| WO | WO 01/15715 A2 | 3/2001 |
| WO | WO 01/17365 A1 | 3/2001 |
| WO | WO 01/45721 A1 | 6/2001 |
| WO | WO 01/97822 A1 | 12/2001 |
| WO | WO 02/28402 A1 | 4/2002 |
| WO | WO 03/057210 A1 | 7/2003 |
| WO | WO 03/068250 A1 | 8/2003 |
| WO | WO 03/070203 A1 | 8/2003 |
| WO | WO 03/070260 A1 | 8/2003 |
| WO | WO 03/071883 A1 | 9/2003 |
| WO | WO 03/099037 A1 | 12/2003 |
| WO | WO 2004/052462 A1 | 6/2004 |
| WO | WO 2004/112509 A2 | 12/2004 |
| WO | WO 2005/030230 A1 | 4/2005 |
| WO | WO 2005/058255 A1 | 6/2005 |
| WO | WO 2006/000992 A1 | 1/2006 |
| WO | WO 2006/037922 A1 | 4/2006 |
| WO | WO 2006/050768 A1 | 5/2006 |
| WO | WO 2007/015027 A1 | 2/2007 |
| WO | WO 2007/112996 A2 | 10/2007 |

OTHER PUBLICATIONS

Gordon et al., "Mast cells as a source of both preformed and immunologically inducible TNF-α/cachectin," *Nature*, vol. 346, Jul. 19, 1990, pp. 274-276, Nature Publishing Group.

Marks et al., "Arachidonic acid metabolism as a reporter of skin irritancy and target of cancer chemoprevention," *Toxicology Letters*, vol. 96, 1998, pp. 111-118, Elsevier.

Murphy et al., "Interleukin-1 and Cutaneous Inflammation: A Crucial Link Between Innate and Acquired Immunity," *Dermatology Foundation: Progress in Dermatology*, vol. 114, No. 3, Mar. 2000, pp. 602-608, The Society for Investigative Dermatology, Inc.

Larrick et al., "Activated Langrehans Cells Release Tumor Necrosis Factor," *Journal of Leukocyte Biology*, vol. 45, 1989, pp. 429-433, Alan R. Liss, Inc.

Groves et al., "Effect of In Vivo Interleukin-1 on Adhesion Molecule Expression in Normal Human Skin," *The Journal of Investigative Dermatology*, vol. 98, No. 3, Mar. 1992, pp. 384-387, The Society for Investigative Dermatology, Inc.

Holliday et al., "Differential Induction of Cutaneous TNF—αand IL-6 by Topically Applied Chemicals," *American Journal of Contact Dermatitis*, vol. 8, No. 3, Sep. 1997, pp. 158-164, W.B. Saunders Company.

Kalliomäki et al., "Probiotics in primary prevention of atopic disease: a randomised placebo-controlled trial," *The Lancet*, vol. 357, Apr. 7, 2001, pp. 1076-1079, The Lancet Publishing Group.

Isolauri et al., "Probiotics in the management of atopic eczema," *Clinical and Experimental Allergy*, vol. 30, 2000, pp. 1604-1610, Blackwell Science Ltd.

Nov. 9, 2009 French Search Report issued in French Patent Application No. 0951362 (with English translation).

Aug. 8, 2007 Office Action issued in U.S. Appl. No. 11/159,198.

Apr. 28, 2008 Office Action issued in U.S. Appl. No. 11/159,198.

Jan. 8, 2009 Office Action issued in U.S. Appl. No. 11/159,198.

Sep. 14, 2009 Notice of Allowance issued in U.S. Appl. No. 11/159,198.

Oct. 14, 2011 Office Action issued in U.S. Appl. No. 12/200,426.

Apr. 15, 2008 International Search Report issued in French Application No. 0757348.

Lin et al., J. Agric. Food Chem. 1999, 47, 1460-1466.

Miyazaki et al., J. Cosmet. Sci., 55, 473-479 (Sep./Oct. 2004).

Dec. 13, 2011 Office Action issued in U.S. Appl. No. 12/607,142.

Pierard-Franchimont et al., International Journal of Cosmetic Science, 2002, 24, 249-256.

Gupta et al., J. Am. Acad. Dermatol. 2004, 51 (5), 785-798.

Kragballe, Curr. Probl. Dermatol. 2009, vol. 38, 160-171.

Nov. 18, 2011 Office Action issued in U.S. Appl. No. 12/659,597.

Paragh, et al. "Novel Sphingolipid Derivatives Promote Keratinocyte Differenciation, "Experimental Dermatology, vol. 17, No. 12, Mar. 17, 2008 (pp. 1004-1016) XP002543996.

Hall et al., "The Generation of Neuronal Heterogeneity in a Rat Sensory Ganglion, "The Journal of Neuroscience, vol. 17, No. 8, pp. 2775-2784, Apr. 15, 1997.

Green et al., "Measuring the Chemosensory Irritability of Human Skin,"Journal of Toxicology Cutaneous and Ocular toxicology, vol. 14, No. 1, pp. 23-48, 1995.

Martin Leverkus et al.; "Post-Transcriptional Regulation of UV Induced TNF—a Expression", The Society for Investigative Dermatology, Inc., 1998, pp. 353-357.

Apr. 15, 2008 Search Report issued in French Application No. 0757352.

Jul. 20, 2011 Office Action issued in U.S. Appl. No. 12/685,697.

Feb. 23, 2012 Office Action issued in U.S. Appl. No. 12/685,697.

Nov. 25, 2011 Office Action issued in U.S. Appl. No. 12/200,417.

Aug. 17, 2011 Office Action issued in U.S. Appl. No. 11/989,694.

Jan. 19, 2012 Office Action issued in U.S. Appl. No. 11/989,694.

Nov. 10, 2011 Office Action issued in U.S. Appl. No. 12/204,437.

Jun. 20, 2008 Office Action issued in U.S. Appl. No. 11/241,964.

Jun. 4, 2009 Office Action issued in U.S. Appl. No. 11/241,964.

Apr. 28, 2005 Search Report issued in French Application No. 0452258.

Sep. 19, 2011 Third Party Observation filed by the Council of Scientific & Industrial Research concerning the equivalent Canadian Patent Application CA 2 697 735 with Annex-1 and Annex-II.

Ayurveda Sarasamgrahah—Shri Baidyanath Ayurveda Bhavan Limited, Calcutta, Edn. 2003 p. 485 Formulation ID: RG12/891B Formulation Name: Vijay Parpati Anupana Evam Upayoga (with English translation) (Exhibit 1).

Mohammad Azam Khan; Muheet Azam vol. II (Part II) (19th century AD), Matba Nizami, Kanpur, 1898 AD p. 55, Formulation ID: AA26/148A1, Formulation Name: Zimaad Bara-e-kalaf (with English translation) (Exhibit 2).

Vagabhata; Astanga Hrdaya—(commentary by Arunadutta) edited by Bhisagacarya Harisastri Paradakara vaidya: Chaukhamba Orientalia, Varanasi, edn. 8th. 1998 [Time of origin 5th century] p. 892, Formulation ID: RS23/1719E, Formulation Name: Vyanganasaka Lepa (with English translation) (Exhibit 3).

Abdulla Sahib; Anuboga Vaithiya Navaneetham, Pub: Palani Thandayuthapani Devasthanam publications, Directorate of Indian systems of Medicine, Chennai. (1975). p. 91, Formulation ID: PD01/79, Formulation Name: Naga Parpam (with English translation) (Exhibit 4).

Ziya Al- Din Abdullah Ibn Al- Baitar; Al-Jaam'e-li Mufradaat-al-Advia-wal-Aghzia, vol. IV (13th century AD), Matba Amra, Cairo, Egypt, 1874 AD p. 57, Formulation ID: MH2/93, Formulation Name: Karm-e Barri (with English translation) (Exhibit 5).

Smkaradajisastripade; Aryabhisaka—Gujarati Edited (Hindustana No Vaidyaraja) Translation by Harikrishna Bhagwan Lal Vyas; Sastu Sahitya Vardhaka Karyalaya, Bhadra, Ahmedabad, Edn. 12th, 1957 p. 168, Formulation ID: RG/173, Formulation Name: Draksadicurnam (05) (with English translation) (Exhibit 6).

Abu Ali lbn-e-Sina; Al-Qaanoon-fil-Tibb, vol. II (11$^{th}$ century AD), Institute of History of Medicine and Medical Research, Jamia Hamdard, New Delhi-62, 1987 AD p. 344, Formulation ID: AHI/603A, Formulation Name: Dawa-e- Kuzbura (with English translation) (Exhibit 7).

Basavaraja; Basavarajiyam-Chaukhambha Sanskrit Pratisthan, Delhi;Edn. 1$^{st}$ Reprint; 2005 [Time of origin 15$^{th}$ century] p. 90, Formulation ID: VK1/176, Formulation Name: Jophesu Pathyam (with English translation) (Exhibit 8).

Abdulla Sahib; Anuboga Vaithiya Navaneetham, Pub: Palani Thandayuthapani Devasthanam publications, Directorate of Indian Systems of Medicine, Chennai. (1975). p. 109, Formulation ID: KS01/127, Formulation Name: Thiraatchaathi Nei—2 (with English translation) (Exhibit 9).

Mohammad Akbar Arzani; Qaraabaadeen Qaadri (17$^{th}$ century AD), Ahamadi Publication, Delhi, 1968 AD p. 3-4, Formulation ID: MH5/01, Formulation Name: Itrifal Sagheer (with English translation) (Exhibit 10).

Mohammad Shareef Khan; Ilaaj al-Amraaz (18$^{th}$ century AD), Afzal-al-Matabe, Barqi Press, Delhi, 1921 AD p. 33, Formulation ID: MH1/287, Formulation Name: Majoon Mufarreh-1 (with English translation) (Exhibit 11).

U.S. Appl. No. 11/241,964 in the name of Gueniche et al., Oct. 4, 2005.

U.S. Appl. No. 11/989,694 in the name of Breton et al., Jan. 30, 2008.

U.S. Appl. No. 12/204,437 in the name of Gueniche et al., Sep. 4, 2008.

U.S. Appl. No. 12/200,426 in the name of Castiel et al., Aug. 28, 2008.

U.S. Appl. No. 12/200,417 in the name of Castiel et al., Aug. 28, 2008.

U.S. Appl. No. 12/607,142 in the name of Gueniche et al., Oct. 28, 2009.

U.S. Appl. No. 12/607,170 in the name of Gueniche et al., Oct. 28, 2009.

U.S. Appl. No. 12/659,597 in the name of Castiel et al., Oct. 28, 2009.

U.S. Appl. No. 12/685,697 in the name of Amar et al., Jan. 12, 2010.

Nov. 17, 2009 International Search Report issued in International Patent Application No. PCT/IB09/053204.

U.S. Appl. No. 13/056,344 in the name of Castiel et al. filed Jan. 28, 2011.

J. Saavedra, et al., "Effect of Long Term Consumption of Infant Formulas with Bifidobacteria (B) and S. Thermophilus (St) on Stool Patterns and Diaper Rash in Infants," Journal of Pediatric Gastroenterology & Nutrition, Oct. 1998, vol. 27, Issue 4, Abstract.

Audrey Nosbaum et al., "Allergic and irritant contact dermatitis," EJD, vol. 19, No. 4, Jul.-Aug. 2009, pp. 325-332.

Avrelija Cenčič, et al., "Functional cell models of the gut and their applications in food microbiology—A review," International Journal of Food Microbiology, 2010, pp. 1-11.

Office Action dated May 8, 2012 in U.S. Appl. No. 12/200,426.

Jan. 4, 2008 Office Action issued in U.S. Appl. No. 11/241,964.

Jan. 13, 2009 Office Action issued in U.S. Appl. No. 11/241,964.

Feb. 5, 2010 Office Action issued in U.S. Appl. No. 11/241,964.

May 2, 2011 Office Action issued in U.S. Appl. No. 12/204,437.

May 18, 2011 Office Action issued in U.S. Appl. No. 12/607,142.

Jul. 13, 2012 Office Action issued in U.S. Appl. No. 12/200,417.

Jul. 17, 2012 Office Action issued in U.S. Appl. No. 13/330,197.

U.S. Appl. No. 11/159,198 in the name of Breton et al., filed Jun. 23, 2005.

Jan. 16, 2007, International Search Report issued in French Patent Application No. PCT/FR2006/050768.

English Translation of WO2006037922 by EPO dated Apr. 14, 2011, p. 1-7.

Nov. 17, 2009 Search Report issued in International Patent Application No. PCT/IB2009/053204.

Ming O. Li, Contextual Regulation of Inflammation: A Duet by Transforming Growth Factor-β and Interleukin-10, Immunity, Apr. 2008, pp. 468-476, vol. 28.

Mary A. Perkins, et al., A noninvasive method to assess skin irritation and compromised skin conditions using simple tape adsorption of molecular markers of inflammation, Skin Research and Technology, Nov. 2001, 2 pages, vol. 7, issue 4.

U.S. Appl. No. 13/514,824, filed Jun. 8, 2012.

U.S. Appl. No. 13/514,872, filed Jun. 8, 2012.

U.S. Appl. No. 13/330,197, filed Dec. 19, 2011.

U.S. Appl. No. 13/471,730, filed May 5, 2012.

Mar. 28, 2013 Office Action issued in. U.S. Appl. No. 13/514,824, filed Jul. 24, 2012.

Apr. 10, 2013 Office Action issued in U.S. Appl. No. 13/330,197, filed Dec. 19, 2011.

Apr. 30, 2013 Office Action issued in U.S. Appl. No. 13/514,872, filed Jul. 24, 2012.

* cited by examiner

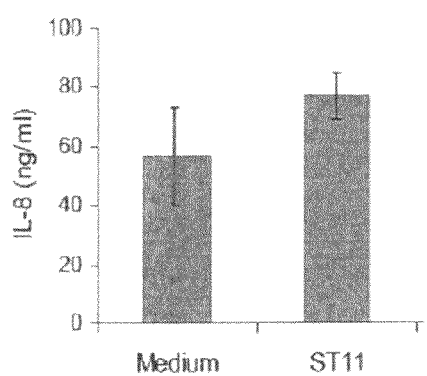

USE OF PROBIOTIC MICROORGANISMS TO LIMIT SKIN IRRITATION

BACKGROUND

Human skin is composed of two compartments, namely a deep compartment, the dermis, and a superficial compartment, the epidermis.

The skin constitutes a barrier against external aggressions, especially those of chemical, mechanical or infectious type, and, there are certain number of reactions which take place therein, these being defence reactions against environmental factors (climate, ultraviolet radiation, tobacco, etc.) and/or xenobiotics, for example microorganisms. This property, referred to as the barrier function, is provided principally by the most superficial layer of the epidermis, namely the horny layer, called the stratum corneum.

It is clear that the quality of the skin barrier and of the mucous membranes is affected daily following external aggressions by irritant agents (detergents, acids, bases, oxidants, reductants, concentration solvents, gases or toxic fumes), mechanical stresses (friction, impacts, abrasion, tearing of the surface, dust projection, particle projection, shaving or hair removal) or thermal or climatic imbalances (cold, dryness).

Skin irritation is conventionally defined as a local, reversible and non-immunological, inflammatory reaction characterized by oedema and erythema, which is induced after single or repeated contact of a chemical substance with the skin.

Substances belonging to different classes of very different chemical products, such as keratinic solvents, dehydrating agents or oxidant or reductant agents, may be considered to be irritants.

Irritation of the skin is a very significant phenomenon, representing as it does, approximately, between 60% and 80% of clinical cases of non-allergic contact dermatitis. The majority of the other cases represent allergic contact dermatitis.

Irritant contact dermatitis (ICD) is a multi-factor disease, triggered as a function of both intrinsic and extrinsic factors. Age, genetic background and sex are also factors which may influence the development of this pathology.

Acute irritant contact dermatitis (ICD) is characterized principally by inflammation, whereas chronic ICD is characterized by hyperproliferation of keratinocytes and by transitory hyperkeratosis.

The biochemical events involved in skin irritation are complex and very little described.

It is known that skin irritation involves a cascade of reactions which, via the recruitment of infiltrating blood cells (neutrophils, macrophages, Langerhans cells) and the substances that they release (cytokines, lymphokines, chemokines, etc.), gives rise to the persistent irritant process which is characterized primarily in irritation of the skin.

The penetration of the skin by chemical compounds is a major parameter in the establishment of the physiopathology of ICD. The latter is associated with the degree of permeability of the skin (which is linked to its physiological condition) and with physicochemical properties of the compounds whose ingress it is thought to restrict (molecular weight, polarity, ionization state) and with the nature of the environment (excipient, vehicle) via which these substances are brought into contact with the skin.

This inevitable step corresponds, on the basis of the external medium or the vehicle, to the release of the molecule which is to diffuse, and therefore to its provision to the body.

In the case of contact between an irritant and the skin, the keratinocytes are the first cells to be activated by the chemical product. The majority of studies into ICD have therefore focused on this type of cell, and numerous data have since become known with regard to their involvement in the physiopathology of ICD. The keratinocytes play an important part in initializing the inflammatory skin reaction, through the release of numerous mediators and cytokines, which underlie a whole cascade of inflammation, ending in the clinical signs of ICD. Among these, IL-1α and derivatives of arachidonic acid possess particular importance in the development of inflammation. Whereas a major part is played by oxidative stress, the part of TNF-α appears to be more controversial.

The release of IL-1α induces, via the activation of the transcription factor NF-kB, the transcription of genes involved in inflammation, such as cytokines IL-1α, IL-6, GM-CSF, TNF-α, chemokines including IL-8, MCP-1, MIP-1α and eotaxin, and also the expression of adhesion molecules such as E-selectin, ICAM-I and VCAM-I (Gordon J R, Nature 1990: 346 (6281): 274-276).

The signalling cascade generated from the activation of the keratinocytes begins from the release of prestored key mediators. In fact, resting keratinocytes contain a large amount of preformed and biologically active IL-1α (Marks F et al., Toxicol Lett 96: 111-118, 1998), and also of arachidonic acid (Murphy J E et al., J Invest Dermatol 114: 602-608, 2000).

Because these two compounds are produced constitutively by keratinocytes, and remain stored in the cell, the epidermis may be considered to be a major reservoir of highly inflammatory mediators. Impairment of the keratinocytes owing to the corrosive effect of a chemical compound, a burn, or by UV exposure automatically induces the release of IL-1α and of arachidonic acid, which become the first defence events of the body.

Accordingly, IL-1α and arachidonic acid might be considered to be the key mediators in triggering irritation in response to a chemical stress (Murphy J E et al., J Invest Dermatol, 114: 602-608, 2000).

Among all of the mediators of information, apart from IL-1 and arachidonic acid, only TNF-α is able to activate a sufficient number of mechanisms to generate skin inflammation independently. This major cytokine of skin inflammation is already prestored in the dermal mastocytes (Larrick J W et al., J Leukoc Biol, 45: 429-433, 1989), but it is also produced by the keratinocytes and the Langerhans cells after stimulation (Groves R W, et al., J Invest Dermatol, 98: 384-387, 1992). One of the mechanisms via which TNF-α exerts the most influence on the inflammatory reaction is the induction of adhesion molecules in synergy with IL-1. Adhesion molecules play an essential part in the circulation and penetration of leukocytes (especially neutrophils) from the peripheral blood vessels to the dermis and epidermis (Holliday M R et al., Am J Contact Dermat, 8: 158-164, 1997).

Numerous chemical products may induce skin irritation; however, they differ in their capacity to generate pro-inflammatory cytokines, and skin inflammation is not systematically dependent on the production of TNF-α.

It is important to note as well that the production of IL-12 and of IL-18 by the activated macrophages at the site of the inflammation plays an important part as a local amplification loop. This is because these cytokines stimulate the production of IFN-α by neighbouring T lymphocytes, which is, in turn, a powerful coactivation factor for the macrophages and the keratinocytes.

Finally, with regard to exogenous stress, it is known that, under particular circumstances, topical compounds may result in the appearance of skin reactions, when they are used in cosmetic or dermatological compositions—for other effects, of course.

Accordingly, cosmetic compositions are used that contain, for example, active keratolytic and/or desquamating agents for combating ageing, and especially active exfoliants and/or active agents which promote cell renewal, such as α-hydroxy acids (especially lactic, glycolic or citric acids), β-hydroxy acids (especially salicylic or n-octanoyl-5-salicylic acids), and retinoids (especially all-trans or 13-cis retinoic acid and retinol). Unfortunately, if these active agents are used in excessive quantities, they can provoke skin irritation. Generally speaking, the skin disorders referred to above are most frequent in the most exposed areas of the body, namely the hands, feet, face, and scalp.

They may occur in particular in areas which are subject to certain operations of daily, or frequently repeated, hygiene, such as shaving, hair removal, cleaning with toilet products or household products, application of adhesives (plasters, patches, attachment of prostheses), or in the case of actions involved in sport, in work or simply associated with lifestyle and with the use of clothing, tools or equipment that gives rise to localized friction. They may also be amplified by psychological stress.

Consequently, it would appear to be valuable to have an effective active agent available for preventing and/or treating and/or reducing these disorders, and more particularly the skin irritation.

SUMMARY

It has now been found, entirely surprisingly, that the use of a microorganism of the genus *Lactobacillus* sp. and/or *Bifidobacterium* species or of a fraction thereof provides satisfaction in these terms.

Accordingly, according to a first aspect, the invention provides for the cosmetic use of an effective amount of at least one probiotic microorganism especially of the genus *Lactobacillus* sp. and/or *Bifidobacterium* sp., of a fraction thereof and/or of a metabolite thereof, as an active agent for limiting skin irritation.

As is apparent from the examples below, the microorganisms in question according to the invention prove to be especially useful for maintaining one or more mechanisms which are conducive to the regulation of skin irritation.

The invention is further directed to the use of an effective amount of at least one probiotic microorganism according to the invention, especially of the genus *Lactobacillus* sp. and/or *Bifidobacterium* sp., of a fraction thereof and/or of a metabolite thereof, as an active agent for preparing a composition intended for preventing the manifestation and/or treating irritative skin disorders.

The invention further provides for the cosmetic use, preferably topically, of an effective amount of at least one probiotic microorganism according to the invention, especially of the genus *Lactobacillus* sp. and/or *Bifidobacterium* sp., and more particularly of the strain of *Lactobacillus paracasei* ST11, of a fraction thereof and/or of a metabolite thereof, as an active agent intended for preventing the manifestation and/or treating irritant contact dermatitis (ICD).

The present invention further provides, in another of its aspects, a cosmetic treatment method for preventing and/or treating irritative skin disorders, especially irritated skin, and more particular irritant contact dermatitis (ICD), comprising the administration, especially orally or topically, of an effective amount of at least one microorganism belonging to the species *Lactobacillus paracasei*, a fraction thereof, or a metabolite thereof.

BRIEF DESCRIPTION OF FIGURE

FIG. 1: illustrates the amount of IL-8 measured at the end of Example 2 in the supernatants by co-culturing the system with medium alone (Medium) or with addition of *Lactobacillus paracasei* ST 11 (ST 11).

DETAILED DESCRIPTION OF EMBODIMENTS

To the knowledge of the inventors, this efficacy of a probiotic microorganism, especially of the genus *Lactobacillus* sp. and/or *Bifidobacterium* sp., of a fraction thereof and/or of a metabolite thereof, has never been described.

The use of microorganisms, especially probiotic microorganisms, for skin care has already been described.

Document WO 2006/037922 describes compositions intended for the treatment of sensitive skin and employing, as an active agent, a combination of a *Lactobacillus paracasei* or casei microorganism and a *Bifidobacterium longum* or *Bifidobacterium lactis* microorganism.

FR 2 872 047 in turn describes a combination of a probiotic microorganism with a divalent inorganic cation.

FR 2 889 057, for its part, discloses a topical composition comprising a probiotic microorganism in combination with a polyunsaturated fatty acid and/or a polyunsaturated fatty acid ester, which is useful for the treatment of sensitive skin.

WO 02/28402 describes the use of probiotic microorganisms for regulating reactions of skin hypersensitivity, namely allergic reactions.

Lastly, WO 03/070260 relates to the use of probiotic microorganisms for purposes of protecting the skin from light.

However, none of these documents describes the use of probiotic microorganisms according to the invention, especially of the genus *Lactobacillus* sp. and/or *Bifidobacterium* sp., and more particularly of the strain *Lactobacillus paracasei* ST11, of a fraction thereof and/or of a metabolite thereof, as an active agent useful in the context of skin irritation disorders.

As is apparent from the tests set out below, after administration for a prolonged period of a microorganism in accordance with the invention, a regulation of skin irritation—and especially its limitation—is observed.

In particular, the inventors have demonstrated that a microorganism of this kind is able selectively to stimulate the production of the regulatory cytokine IL-8.

Accordingly, the compositions which comprise at least one microorganism in accordance with the invention may be intended for preventing and/or reducing the manifestation of the cutaneous signs of irritative type, especially those induced by exogenous stress of chemical, environmental or mechanical origin.

Skin irritation may be induced in particular by at least one condition selected from the action of chemical products, of compounds capable of causing irritation to the skin, of temperature, of the climate, of atmospheric pollution or of friction.

In one preferred version, the stress considered according to the invention is different from that inherent in a hair removal or peeling operation.

In particular, the microorganisms in accordance with the present invention may be employed as an anti-irritant agent.

The skin irritation considered within the invention does not rely upon any immunological component, and as such is distinct for example, from psoriasis, contact hypersensitivity or delayed contact hypersensitivity.

The skin irritation considered in the invention is in particular a non allergic skin irritation. More particularly, the instant invention relates to prevent and/or treat non allergic irritant contact dermatitis.

The invention thus likewise provides, in another of its aspects, for the cosmetic use of at least one effective amount of at least one probiotic microorganism especially of the genus *Lactobacillus* sp. and/or *Bifidobacterium* sp., of a fraction thereof and/or a metabolite thereof as an agent for reinforcing the protection of the skin towards external aggressions.

It is directed more particularly to the cosmetic use of an effective amount of at least one probiotic microorganism especially of the genus *Lactobacillus* sp. and/or *Bifidobacterium* sp., of a fraction thereof and/or of a metabolite thereof for preventing the skin irritation that may be induced by one or more external aggressions in the form of irritant agents such as, for example, detergents, acids, bases, oxidants, reductants, concentrated solvents, gases or toxic fumes, with regard to one or more mechanical stresses such as, for example, friction, impacts, abrasion, tearing of the surface, projection of dust, projection of particles, and shaving, or in relation to thermal or climatic imbalance(s) such as, for example, the cold.

Accordingly, it is directed to the cosmetic use of an effective amount of a lysate of at least one probiotic microorganism especially of the genus *Lactobacillus* sp. and/or *Bifidobacterium* sp., of a fraction thereof and/or of a metabolite thereof for preventing and/or treating irritative skin disorders which follow exposure to atmospheric pollutants.

The invention is directed, moreover, to the cosmetic use of an effective amount of at least one probiotic microorganism especially of the genus *Lactobacillus* sp. and/or *Bifidobacterium* sp., of a fraction thereof and/or of a metabolite thereof for preventing and/or treating irritative skin disorders generated by oxidative stress initiated by an environmental oxidant, such as, for example, oxygen, ozone and/or nitrogen oxides and sulphur oxides.

An "effective amount" in the sense of the present invention is an amount which is sufficient to produce the expected effect.

In the sense of the present invention, the term "to prevent" means to reduce the risk of manifestation of the phenomenon in question.

This reduction may lead to a lower degree of risk than that existing prior to the use according to the invention.

In the sense of the present invention, the term "to treat" means to remedy a physiological dysfunction, and more generally to reduce or even suppress the undesirable disorder whose manifestation is, in particular, a consequence of said dysfunction.

In the sense of the invention, the term "to limit" with regard to a symptom, means reducing the intensity of expression of that symptom, for example a skin irritation, and/or reducing the risk of that symptom occurring.

It will be appreciated that the reduction in the intensity and/or risk in question may be complete or partial, i.e. the risk of the symptom occurring, or the intensity of its expression, remains, but to a lesser extent than before the use according to the invention.

According to one embodiment of the invention, a microorganism according to the invention may be employed orally.

According to another embodiment of the invention, the microorganism according to the invention may be employed topically.

Topical products nevertheless act, by definition, locally in the areas to be treated; in these areas, they may be distributed unequally, and necessitate careful and repeated applications.

In contrast, the oral route has the advantage of acting globally in the entire skin, including its deep layers (dermis, hypodermis), in accordance with a means of administration which is rapid and relatively unconstricting. Indeed, the metabolites and other active nutrients are distributed, in particular, within the dermal matrix via the blood stream.

The oral route or administration by patch also have the advantage of a means of administration which is rapid and relatively unconstricting.

According to one preferred embodiment, the cosmetic use according to the invention is therefore practised orally, and the method according to the invention comprises orally administering said effective amount of the microorganism in question, according to the invention, or a fraction thereof, or a metabolite thereof.

As specified below, the compositions comprising said microorganism are formulated so as to be compatible with the method of administration that is employed.

Microorganisms

A microorganism suitable for the invention is a probiotic microorganism, especially of the genus *Lactobacillus* sp. and/or *Bifidobacterium* sp.

For the purposes of the present invention, a "probiotic microorganism" is a living microorganism which, when it is consumed in appropriate amount, has a positive effect on the health of its host (*Joint FAO/WHO Expert Consultation on Evaluation of Health and Nutritional Properties of Probiotic in Food Including Powder Milk with Live Lactic Acid Bacteria*, 6 Oct. 2001), and which may in particular enhance the intestinal microbial balance.

According to one variant of the invention, this microorganism is employed in an isolated form, i.e. not mixed with one or more compounds that may be associated with said microorganism in its original environment.

For the purposes of the invention, the term "metabolite" denotes any substances obtained from the metabolism of the microorganisms in question according to the invention and also endowed with efficacy in the treatment of irritated skin.

For the purposes of the invention, the term "fraction" denotes more particularly a fragment of said microorganism that is effective in treating oily skin or skin with an oily tendency, by analogy with said microorganism in its whole form.

Specific examples of probiotic microorganisms suitable for the invention are *Bifidobacterium adolescentis, Bifidobacterium animalis, Bifidobacterium bifidum, Bifidobacterium breve, Bifidobacterium lactis, Bifidobacterium longum, Bifidobacterium infantis, Bifidobacterium pseudocatenulatum, Lactobacillus acidophilus* (NCFB 1748); *Lactobacillus amylovorus, Lactobacillus casei* (Shirota), *Lactobacillus rhamnosus* (strain GG), *Lactobacillus brevis, Lactobacillus crispatus, Lactobacillus delbrueckii* (subsp *bulgaricus, lactis*), *Lactobacillus fermentum, Lactobacillus helveticus, Lactobacillus gallinarum, Lactobacillus gasseri, Lactobacillus johnsonii* (CNCM 1-1225), *Lactobacillus plantarum, Lactobacillus reuteri, Lactobacillus salivarius, Lactobacillus alimentarius, Lactobacillus curvatus, Lactobacillus casei* subsp. *casei, Lactobacillus sake, Lactococcus lactis, Enterococcus (faecalis, faecium), Lactococcus* lactis (subspp *lactis* or *cremoris*), *Leuconostoc mesenteroides* subsp *dextranicum, Pediococcus acidilactici, Sporolactobacillus inulinus, Streptococcus salvarius* subsp. *thermophilus, Streptococcus thermophilus, Staphylococccus carnosus, Staphylococcus xylosus, Saccharomyces* (*cerevisiae* or else *boulardii*), *Bacillus*

(*cereus var toyo* or *subtilis*), *Bacillus coagulans, Bacillus licheniformis, Escherichia coli* strain nissle, *Propionibacterium freudenreichii*, and mixtures thereof.

More particularly, the probiotic microorganisms may be obtained from the group of lactic acid bacteria, such as, in particular, *Lactobacillus* and/or *Bifidobacterium* bacteria.

As illustrations of these lactic acid bacteria, mention may be made more particularly of the bacteria *Lactobacillus johnsonii, Lactobacillus reuteri, Lactobacillus rhamnosus, Lactobacillus paracasei, Lactobacillus casei, Bifidobacterium bifidum, Bifidobacterium breve, Bifidobacterium longum, Bifidobacterium animalis, Bifidobacterium lactis, Bifidobacterium infantis, Bifidobacterium adolescentis, Bifidobacterium pseudocatenulatum*, and mixtures thereof.

The species that are especially suitable are the bacteria *Lactobacillus johnsonii, Lactobacillus paracasei, Bifidobacterium adolescentis, Bifidobacterium longum* which were deposited, respectively, in accordance with the Treaty of Budapest, with the Institut Pasteur (28 rue du Docteur Roux, F-75024 Paris cedex 15) on Jun. 30, 1992, Jan. 12, 1999, Apr. 15, 1999 and Apr. 15, 1999 under the following designations—CNCM I-1225, CNCM I-2116, CNCM I-2168 and CNCM I-2170, *Bifidobacterium lactis* (Bb 12) (ATCC27536) or *Bifidobacterium longum* (BB536). The strain of *Bifidobacterium lactis* (ATCC27536) may be obtained from Hansen (Chr. Hansen A/S, 10-12 Boege Alle, P.O. Box 407, DK-2970 Hoersholm, Denmark).

According to one embodiment, a probiotic microorganism suitable for the invention may more particularly be a microorganism of the genus *Lactobacillus* sp.

With preference, a microorganism of the genus *Lactobacillus* sp. which is suitable for the invention may be selected from the species *Lactobacillus johnsonii, Lactobacillus reuteri, Lactobacillus rhamnosus, Lactobacillus paracasei, Lactobacillus casei*, and mixtures thereof.

According to one preferred embodiment, a microorganism suitable for the invention may be a *Lactobacillus paracasei*.

A microorganism suitable for the invention may more particularly be the *Lactobacillus paracasei* strain deposited in accordance with the Treaty of Budapest at the Institut Pasteur (28 rue du Docteur Roux, F-75024 Paris cedex 15) on Dec. 1, 1999 under the designation CNCM I-2116, and/or a fraction thereof and/or a metabolite thereof.

According to one embodiment, the invention relates to the use, in addition to a first probiotic microorganism, as defined above, and especially of the genus *Lactobacillus* and/or *Bifidobacterium* sp., of at least an effective amount of at least one second microorganism, especially of probiotic type, and/or a fraction thereof and/or a metabolite thereof, which is different from said first microorganism.

This second microorganism may be selected in particular from ascomycetes such as *Saccharomyces, Yarrowia, Kluyveromyces, Torulaspora, Schizosaccharomyces pombe, Debaromyces, Candida, Pichia, Aspergillus* and *Penicillium*, bacteria of the genus *Bacteroides, Fusobacterium, Melissococcus, Propionibacterium, Enterococcus, Lactococcus, Staphylococcus, Peptostrepococcus, Bacillus, Pediococcus, Micrococcus, Leuconostoc, Weissella, Aerococcus, Oenococcus, Lactobacillus, Bifidobacterium*, and mixtures thereof.

Ascomycetes which are very suitable for the present invention include, in particular, *Yarrowia lipolitica* and *Kluyveromyces lactis*, and also *Saccharomyces cereviseae, Torulaspora, Schizosaccharamyces pombe, Candida* and *Pichia*.

Specific examples of probiotic microorganisms are *Lactobacillus acidophilus, Lactobacillus alimentarius, Lactobacillus curvatus, Lactobacillus delbruckii* subsp. *lactis, Lactobacillus gasseri, Lactobacillus johnsonii, Lactobacillus reuteri, Lactobacillus rhamnosus* (*Lactobacillus* GG), *Lactobacillus sake, Lactococcus lactis, Streptococcus thermophilus, Staphylococccus carnosus, Staphylococcus xylosus*, and mixtures thereof.

According to one embodiment, the following yeast and bacterial genera are used preferentially as a second microorganism:

lactic acid bacteria, which produce lactic acid by fermentation of sugar. Depending on their morphology, they are divided into two groups:

*Lactobacillus* species: *Lactobacillus acidophilus, amylovorus, casei, rhamnosus, brevis, crispatus, delbrueckii* (subsp *bulgaricus, lactis*), *fermentum, helveticus, gallinarum, gasseri, johnsonii, plantarum, reuteri, salivarius, alimentarius, curvatus, casei* subsp. *casei*, sake, and Cocci: *Enterococcus* (*faecalis, faecium*), *Lactococcus lactis* (subsp *lactis* or *cremoris*), *Leuconostoc mesenteroides* subsp *dextranicum, Pediococcus acidilactici, Sporolactobacillus inulinus, Streptococcus salvarius* subsp. *thermophilus, Streptococcus thermophilus, Staphylococccus carnosus, Staphylococcus xylosus*, bifidobacteria or *Bifidobacterium* species: *Bifidobacterium adolescentis, animalis, bifidum, breve, lactis, longum, infantis, pseudocatenulatum*, yeasts: *Saccharomyces* (*cerevisiae* or else *boulardii*), the other sporulated bacteria: *Bacillus* (cereus var *toyo* or *subtilis*), *Bacillus coagulans, Bacillus licheniformis, Escherichia coli* strain nissle, *Propionibacterium freudenreichii*, and mixtures thereof.

More particularly, the second microorganism may be one of the probiotic microorganisms proposed above, as a specific example of probiotic microorganisms for the first microorganism.

According to one particular embodiment, the second probiotic microorganism is of the genus *Lactobacillus* species, more particular of the species *Lactobacillus johnsonii*, a fraction thereof and/or a metabolite thereof.

The species in question may in particular be the *Lactobacillus johnsonii* deposited respectively, in accordance with the Treaty of Budapest, at the Institut Pasteur (28 rue du Docteur Roux, F-75024 Paris cedex 15) on Jun. 30, 1992, under the designation CNCM I-1225.

A microorganism of the invention may be formulated in a composition in a proportion of at least 0.0001% (expressed by dry weight), in particular in a proportion of 0.0001 to 20% and more particularly in a proportion of 0.001 to 15% by weight, more particularly of 0.01 to 10% by weight, and especially of 0.1% to 2% by weight, relative to the total weight of the composition.

Generally speaking, a composition according to the invention, and more particularly a composition intended for oral administration, may comprise, in terms of living microorganisms, from $10^3$ to $10^{15}$ cfu/g, in particular from $10^5$ to $10^{15}$ cfu/g and more particularly from $10^7$ to $10^{12}$ cfu/g of microorganisms per gram of vehicle, or at equivalent doses as calculated for the inactive or dead microorganisms or for microorganism fractions or for metabolites produced.

In the particular case of compositions that have to be administered orally, the concentration of each microorganism and/or corresponding fraction and/or corresponding metabolite may be adjusted so as to correspond to doses (expressed as microorganism equivalent) ranging from $5\times10^5$ to $10^{13}$ cfu/d and in particular from $10^8$ to $10^{11}$ cfu/d.

A composition for topical application according to the invention may comprise, generally, from $10^3$ to $10^{12}$ cfu/g, in particular from $10^5$ to $10^{10}$ cfu/g, and more particularly from $10^7$ to $10^9$ cfu/g of microorganisms.

When a composition comprises metabolites, the amounts of metabolites in the compositions correspond substantially to the amounts that may be produced by $10^3$ to $10^{15}$ cfu, in particular $10^5$ to $10^{15}$ cfu, and more particularly $10^7$ to $10^{12}$ cfu, of living microorganisms per gram of vehicle.

The expression of the amount of metabolites or of fractions of a microorganism in "cfu" is intended to denote the amount of this microorganism required for the production of said amount of metabolites or of fractions.

The microorganism or microorganisms may be included in a composition according to the invention in a live, semi-active or inactivated, dead form.

According to one particular embodiment, these microorganisms are employed in a live form.

It or they may also be included in the form of cell component fractions or in the form of metabolites. The microorganism(s), metabolite(s) or fraction(s) may also be introduced in the form of a lyophilized powder, a culture supernatant and/or, where appropriate, in a concentrated form.

According to one variant, the compositions may also comprise a divalent inorganic cation.

In the particular case of topical compositions, it may be advantageous to employ these microrogansims in inactivated or even dead form.

COMPOSITION ACCORDING TO THE PRESENT INVENTION

According to yet another of its aspects, the present invention provides a cosmetic and/or dermatological composition, especially a topical composition, which is useful especially for preventing, reducing and/or treating an irritative skin disorder, and which comprises, in a physiologically acceptable medium, at least one effective amount of at least one probiotic microorganism, especially of the genus *Lactobacillus* sp. and/or *Bifidobacterium* sp., of a fraction thereof and/or of a metabolite thereof, in combination with an effective amount of at least one agent capable of causing irritation of the skin.

Accordingly, according to one of its aspects, the present invention relates to the use of a microorganism of the invention for preventing and/or reducing the irritant effect of a cosmetic or dermatological composition containing one or more compounds capable of causing irritation of the skin.

Among these compounds, mention may be made in particular of cosmetic compounds or actives, dermatological compounds or actives, surfactants, especially anionic surfactants, preservatives, detergents, fragrances, and especially fragrancing alcohol solutions, solvents, propellants, and mixtures thereof.

Other irritant agents that may be mentioned include the following: pyruvic acid, gluconic acid, glucuronic acid, oxalic acid, malonic acid, succinic acid, acetic acid, gentisic acid, cinnamic acid and azelaic acid; phenol; resorcinol; urea and its derivatives, hydroxyethylurea or Hydrovance® from National Starch; oligofucoses; jasmonic acid and its derivatives; ascorbic acid and its derivatives, trichloroacetic acid; extract of Saphora japonica, and resveratrol.

The enzymes involved in desquamation or breakdown of corneodesmosomes may also be capable of causing irritation of the skin.

Other irritant agents that may be mentioned include mineral salt chelating agents such as EDTA; N-acyl-N,N', N'ethylenediaminetriacetic acid; aminosulphonic compounds and more particularly N-2 hydroxyethylpiperazine-N-2-ethanesulphonic acid (HEPES); 2-oxothiazolidine-4-carboxylic acid (procysteine) derivatives; derivatives of alpha-amino acids of glycine type, as described in EP 0 852 949, and also sodium methylglycine diacetate, sold by BASF under the trade name Trilon M®; honey; and sugar derivatives such as O-octanoyl-6-D-maltose, O-linoleyl-6-D-glucose and N-acetyl glucosamine.

Retinoids as well are compounds capable of causing irritation of the skin. They include, for example, retinol and its esters, retinal, retinoic acid and its derivatives, such as those described in documents FR-A-2 570 377, EP-A-0 199 636, EP-A-0 325 540 and EP-A-0 402 072, and adapalene.

The salts and derivatives, such as the cis or trans forms, the racemic mixtures, and the dextrorotatory or laevo rotatory forms of the abovementioned compounds, are also considered to be compounds capable of causing irritation of the skin.

Other dermatological or cosmetic actives capable of causing irritation of the skin are also mentioned hereinafter:
  urea and its derivatives, such as hydroxyethylurea or HYDROVANCE from National Starch;
  certain vitamins such as vitamin D and its derivatives, such as vitamin D3, vitamin D2, calcitriol, calcipotriol, tacalcitol, 24,25-diOH vitamin D3, 1-OH vitamin D2 and 1,24-diOH vitamin D2; vitamin B9 and its derivatives;
  peroxides such as benzoyl peroxide and hydrogen peroxide,
  anti-hair loss agents, such as minoxidil and its derivatives such as aminexil;
  hair dyes and hair colorants, such as aminophenols and their derivatives such as para-phenylenediamine (p-PDA), N-phenyl p-PDA, toluene-2,5-diamine sulphate, meta-phenylenediamine (m-PDA), toluene-3,4-diamine and ortho-phenylenediamine (o-PDA);
  antiperspirants, such as aluminium salts, such as aluminium hydroxychloride;
  deodorants;
  active penning agents such as thioglycolates and aqueous ammonia;
  thioglycolate and salts thereof;
  phenoxyethanol;
  1,2-pentanediol;
  fragrancing alcoholic solutions (fragrances, eaux de toilette, aftershaves and deodorants);
  anthralins (dioxyanthranol);
  anthranoids (for example, those described in document EP-A-0 319 028),
  lithium salts;
  depigmenting agents (e.g. hydroquinone, vitamin C at high concentration, kojic acid);
  certain active slimming agents with a heating effect;
  nicotinates and derivatives thereof;
  capsaicin;
  active antilouse agents (pyrethrine);
  anti-proliferative agents such as 5-fluorouracil or methotrexate;
  antiviral agents;
  antiparasitic agents;
  antifungal agents;
  antipruriginous agents;
  antiseborrhoeic agents;
  certain sunscreens;
  pro-pigmenting agents such as psoralens and methylangecilins;
  and mixtures thereof.

Preservatives include phenoxyethanol, chlorhexidine and benzalkonium chloride.

Surfactants include anionic, cationic and amphoteric surfactants, more particularly anionic surfactants such as alkyl sulphates and alkyl ether sulphates, such as lauryl sulphate and lauryl ether sulphate, and their salts, especially their sodium salts.

The compound more particularly associated is selected from retinoids, α-hydroxy acids, β-hydroxy acids, saturated and unsaturated dicarboxylic acids such as octadecene dioic acid or ARLATONE DIOC DCA, sold by Uniqema, anionic, cationic or amphoteric surfactants, n-octanoyl-5-salicylic acid, active antiperspirants such as aluminium salts, N-2 hydroxyethylpiperazine-N-2-ethanesulphonic acid (HEPES) and cinnamic acid.

The compound capable of causing irritation of the skin may be present in the composition according to the present invention in an amount sufficient to cause a skin irritation reaction. As an example, it may be present in an amount of from 0.0001 to 70% by weight, preferably from 0.01 to 50% by weight and more preferably from 0.1 to 30% by weight, relative to the total weight of the composition.

Additional Active Agents

The microorganisms contemplated according to the invention may also be combined with at least 0.00001% to 95% by weight of an anti-inflammatory agent, another calmative, or a mixture thereof.

Examples of "anti-inflammatory agents" include the following:

an antagonist of inflammatory cytokines;

a steroidal anti-inflammatory (hydrocortisone, betamethasone, dexamethasone, etc);

a non-steroidal anti-inflammatory such as aspirin or paracetamol;

and mixtures thereof.

"Antagonists of inflammatory cytokines" according to the invention means a compound capable of inhibiting the synthesis and/or the release of one or more inflammatory cytokines. Also included in the definition of an antagonist of inflammatory cytokines are compounds which inhibit or block the binding of these cytokines to their receptor(s).

In particular, the other calmative may advantageously be selected from allantoin, beta-glycyrrhetinic acid, extracts containing it, such as, for example, extract of Glycyrrhiza glabra (liquorice), and complexes containing it, such as the allantoin/glycyrrhetinic acid complex; lyophilized or non-lyophilized planktons, extracts thereof and complexes thereof; waters and extracts of flowers and of plants: camomile water lime water, rose water, extracts of birch; bisabolol; essential oils, for example coriander oil; algae, especially of the type Laminaria (for example red or brown algae) such as the brown alga extract Padina pavonica, such as HPS 3 PADINA PAVONICA sold by the company Alban Muller; acexamic acid and transexamic acid (4-trans-amino-methyl-cyclohexane carboxylic acid); ursolic acid and extracts containing it, such as extract of rosemary leaf; polysaccharides containing fucose, such as FUCOGEL 1000, sold by the company Solabia; electrolytes, and more particularly an aqueous mixture such as Dead Sea bath salts; amino acids, such as SEPICALM S and VG from Seppic, and divalent magnesium salts such as magnesium gluconate.

According to one particular embodiment of the invention, the anti-inflammatory agent is selected from algal extracts capable of modulating the production of cytokines by keratinocytes, such as PHYCOSACCHARIDE, sold by the company CODIF, the water/glycol extract of the alga *Laminaria saccharina*, especially PHLOROGINE, sold by the company SECMA, extracts of Aloe vera, the extract of bark and of roots of *Terminalia sericea*, or SERICOSIDE 3058500, sold by the company INDENA.

The anti-inflammatory agents are present preferably in the compositions in accordance with the invention at a concentration which may range between 0.00001% and 10% by weight, approximately, relative to the total weight of the composition. More preferably still, the concentration of anti-inflammatory compound may range between 0.0005% and 2% by weight, relative to the total weight of the composition.

In the topical formulations, active hydrophilic agents that may be used more particularly include proteins or protein hydrolysates, amino acids, polyols, especially $C_2$ to $C_{10}$ polyols such as glycerol, sorbitol, butylene glycol and polyethylene glycol, urea, allantoin, sugars and sugar derivatives, water-insoluble vitamins, starch, and bacterial or plant extracts such as those of aloe vera.

With regard to active lipophilic agents, use may be made of retinol (vitamin A) and its derivatives, tocopherol (vitamin E) and its derivatives, ceramides, essential oils, and unsaponifiable constituents (tocotrienol, sesame, gamma-oryzanol, phytosterols, squalenes, waxes, terpenes).

It is also possible, advantageously, to include active agents which promote desquamation, such as the reference active hydrating agents in cosmetology, such as glycerol, hyaluronic acid, urea and its derivatives, and also active agents which promote desquamation such as chelating agents, jasmonic acid and its derivatives, particularly ER2412, reducing compounds, sulphonic derivatives and especially HEPES, amino acids, AHAs and BHAs, especially glycolic acid and ER195, and certain detergents.

Formulations

The compositions according to the invention may be in any of the formulating forms that are normally available for the method of administration selected.

The vehicle may be of diverse nature depending on the type of composition under consideration. The compositions for topical administration may be aqueous, aqueous-alcoholic or oily solutions, dispersions of the solution type or dispersions of the lotion or serum type, emulsions of liquid or semi-liquid consistency, of the milk type, suspensions or emulsions of the cream type, aqueous or anhydrous gels, microemulsions, microcapsules, microparticles, or vesicular dispersions of ionic and/or nonionic type.

These compositions are prepared according to the usual methods.

These compositions may constitute in particular cleansing, treatment or care creams for the face, for the hands, for the feet, for the major anatomical folds or for the body (for example, day creams, night creams, makeup-removing creams, foundation creams, antisun creams), makeup products such as liquid foundations, makeup-removing milks, protective or care body milks, aftersun milks, skincare lotions, gels or mousses, such as cleansing or disinfecting lotions, antisun lotions, artificial tanning lotions, or bath compositions.

The compositions according to the invention may also consist of solid preparations constituting cleansing soaps or bars.

When the composition of the invention is an emulsion, the proportion of the fatty phase may range from 5% to 80% by weight, and preferably from 5% to 50% by weight, relative to the total weight of the composition. The oils, the emulsifiers and the coemulsifiers used in the composition in emulsion form are selected from those conventionally used in the cosmetics and/or dermatological field. The emulsifier and the coemulsifier may be present, in the composition, in a proportion ranging from 0.3% to 30% by weight, and preferably from 0.5% to 20% by weight, relative to the total weight of the composition.

When the composition of the invention is an oily gel or solution, the fatty phase may represent more than 90% of the total weight of the composition.

In a known manner, the formulations for topical administration may also contain adjuvants that are customary in the cosmetics, pharmaceutical and/or dermatological field, such as hydrophilic or lipophilic gelling agents, hydrophilic or lipophilic active agents, preservatives, antioxidants, solvents, fragrances, fillers, screens, bactericides, odour absorbers and colorants. The amounts of these various adjuvants are those conventionally used in the field under consideration, and are, for example, from 0.01% to 20% of the total weight of the composition. Depending on their nature, these adjuvants may be introduced into the fatty phase and/or into the aqueous phase.

As fats that can be used in the invention, mention may be made of mineral oils such as, for example, hydrogenated polyisobutene and liquid petroleum jelly, plant oils such as, for example, a liquid fraction of shea butter, sunflower oil and apricot kernel oil, animal oils such as, for example, perhydrosqualene, synthetic oils, in particular Purcellin oil, isopropyl myristate and ethylhexyl palmitate, unsaturated fatty acids and fluoro oils such as, for example, perfluoropolyethers. Use may also be made of fatty alcohols, fatty acids such as, for example, stearic acid and such as, for example, waxes, in particular paraffin wax, carnauba wax and beeswax. Use may also be made of silicone compounds such as silicone oils and, for example, cyclomethicone and dimethicone, and silicone waxes, resins and gums.

As emulsifiers that can be used in the invention, mention may, for example, be made of glyceryl stearate, polysorbate 60, the mixture of cetylstearyl alcohol/ethoxyl cetylstearyl alcohol comprising 33 mol of ethylene oxide, sold under the name SINNOWAX AO by the company Henkel, the mixture of PEG-6/PEG-32/glycol stearate sold under the name TEFOSE 63 by the company Gattefosse, PPG-3 myristyl ether, silicone emulsifiers such as cetyl dimethicone copolyol and sorbitan monostearate or tristearate, PEG-40 stearate, or ethoxylated sorbitan monostearate (20 EO).

As solvents that can be used in the invention, mention may be made of lower alcohols, in particular ethanol and isopropanol, and propylene glycol.

A composition of the invention may also advantageously contain a spring and/or mineral water, in particular selected from VITTEL water, waters from the Vichy basin, and LA ROCHE POSAY water.

As hydrophilic gelling agents, mention may be made of carboxylic polymers such as carbomer, acrylic copolymers such as acrylate/alkyl acrylate copolymers, polyacrylamides, and in particular the mixture of polyacrylamide, C13-14 isoparaffin and Laureth-7 sold under the name SEPIGEL 305 by the company SEPPIC, polysaccharides, for instance cellulosic derivatives such as hydroxyalkylcelluloses, and in particular hydroxypropylcellulose and hydroxyethylcellulose, natural gums such as guar, carob and xanthan, and clays.

As lipophilic gelling agents, mention may be made of modified clays such as bentones, metal salts of fatty acids, such as aluminium stearates and hydrophobic silica, or else ethylcellulose and polyethylene.

In the case of a use in accordance with the invention by oral administration, use of an ingestible vehicle is preferred.

The ingestible vehicle may be of diverse nature depending on the type of composition under consideration.

Tables or lozenges, oral supplements in dry form and oral supplements in liquid form are thus in particular suitable for use as pharmaceutical or food vehicles.

They may, for example, be food supplements, the formulation of which may be performed via the usual processes for in particular producing dragees, gel capsules, gels, emulsions, tablets, capsules and hydrogels allowing controlled release.

In particular, the microorganism according to the invention may be incorporated into any other form of food supplement or enriched food, for example food bars or compacted or non-compacted powders. The powders may be diluted in water, soda, milk products or soya bean derivatives, or be incorporated into food bars.

The microorganism, according to the invention, may, moreover, be formulated with the excipients and components that are customary for such oral compositions or food supplements, i.e., in particular, fatty and/or aqueous components, humectants, thickeners, preservatives, texturing agents, flavour enhancers and/or coating agents, antioxidants, preservatives and dyes that are customary in the food sector.

The formulating agents and excipients for oral compositions, and in particular for food supplements, are known in this field and will not be the subject of a detailed description herein.

Milk, yogurt, cheese, fermented milks, milk-based fermented products, ices, cereal-based products or fermented cereal-based products, milk-based powders, infant and baby formulas, food products of confectionery, chocolate or cereal type, animal feed, in particular for domestic animals, tablets, gel capsules or lozenges, liquid bacterial suspensions, oral supplements in dry form and oral supplements in liquid form are especially suitable as pharmaceutical or food vehicles.

A microorganism in accordance with the invention may, moreover, be formulated with the excipients and components that are customary for such oral compositions or food supplements, i.e., in particular, fatty and/or aqueous components, humectants, thickeners, preservatives, texturing agents, flavour enhancers and/or coating agents, antioxidants, preservatives and dyes that are customary in the food sector.

The formulating agents and excipients for oral compositions, and in particular for food supplements, are known in this field and will not be the subject of a detailed description herein. Many embodiments of oral compositions and in particular of food supplements are possible for ingestion. The formulation thereof is carried out by means of the usual methods for producing dragees, gel capsules, gels, hydrogels for controlled release, emulsions, tablets or capsules.

According to one particular embodiment, the ancillary microorganisms under consideration according to the invention may be formulated in compositions in an encapsulated form so as significantly to improve their survival time. In such a case, the presence of a capsule may in particular delay or prevent the degradation of the microorganism in the gastrointestinal tract.

The cosmetic treatment method of the invention may be carried out in particular by orally and/or topically administering at least an effective amount of at least one microorganism in accordance with the invention.

Topical administration comprises the external application, to the skin, of cosmetic and/or dermatological compositions according to the customary technique for using these compositions.

By way of illustration, the cosmetic method according to the invention may be carried out by topical application, for example daily, of the microorganism in accordance with the invention, which may, for example, be formulated in the form of creams, gels, sera, lotions, emulsions, makeup-removing milks or aftersun compositions.

The method according to the invention may comprise a single application. According to another embodiment, the application is repeated, for example, 2 to 3 times a day, for one day or more, and generally for a sustained period of at least 4, or even 1 to 15, weeks.

Oral administration comprises ingesting, in one or more intakes, an oral composition as defined above.

In the description and in the examples which follow, unless otherwise indicated, the percentages are percentages by weight and the ranges of values written in the form "between . . . and . . . " include the upper and lower limits specified. The ingredients are mixed, before they are formulated, in the order and under conditions readily determined by those skilled in the art.

According to one variant, the cosmetic method comprises at least one step of orally administering an effective amount of at least one microorganism according to the invention, or of a fraction thereof, and at least one step of topically administering an effective amount of at least one microorganism according to the invention or of a fraction thereof.

The method according to the invention may comprise a single administration.

According to another embodiment, the administration is repeated, for example, 2 to 3 times a day, for one day or more and generally for a sustained period of at least 4 days, or even 4 to 15 weeks, with, where appropriate, one or more periods of interruption.

In addition, combinations of treatment with, optionally, oral or topical forms may be envisaged in order to supplement or reinforce the activity of the microorganism as defined by the invention.

Thus, a topical treatment with a composition containing a microorganism in accordance with the invention, combined with an oral or topical composition optionally containing another microorganism, in particular a probiotic microorganism, or other probiotics in dead, live or semi-active form could be contemplated.

The ingredients are mixed, before they are shaped, in the order and under conditions readily determined by those skilled in the art.

EXAMPLES

The examples hereinafter are presented by way of non-limiting illustration of the field of the invention.

In these examples, the term "cfu" denotes "colony forming unit". This is the unit of measurement used to quantify live bacteria.

The *Lactobacillus paracasei* used in the compositions of the examples hereinafter is *Lactobacillus paracasei* ST11 NCC 2461 (CNCM I-2116).

Example 1

Examples of Compositions for Oral Administration

Example 1a

Powder Stick

| Active principle | |
| --- | --- |
| *Lactobacillus paracasei* ST11 | $10^{10}$ cfu |
| Excipient | |
| Xanthan gum | 0.8 mg |
| Sodium benzoate | 0.2 mg |
| Maltodextrin | qs 30 g |

One stick per day can be taken.

Example 1b

Powder Stick

| Active principle | |
| --- | --- |
| *Lactobacillus paracasei* ST11 | $10^{10}$ cfu |
| Excipient | |
| Xanthan gum | 0.8 mg |
| Sodium benzoate | 0.2 mg |
| Maltodextrin | qs 30 g |

One stick per day can be taken.

Example 1c

Capsules

| Active principle | mg/capsule |
| --- | --- |
| *Lactobacillus johnsonii* | $10^8$ cfu |
| Vitamin C | 60 |
| Magnesium stearate | 0.02 |

One to three of these capsules can be taken per day.

Example 1d

Dragee Formulation

|  | mg/dragee |
|---|---|
| Active ingredients |  |
| *Lactobacillus paracasei* ST11 | $5 \times 10^8$ cfu |
| *Bifidobacterium longum* | $5 \times 10^8$ cfu |
| Dragee core excipient |  |
| Microcrystalline cellulose | 70 |
| Encompress ™ | 60 |
| Magnesium stearate | 3 |
| Anhydrous colloidal silica | 1 |
| Coating agent |  |
| Shellac | 5 |
| Talc | 61 |
| Sucrose | 250 |
| Polyvidone | 6 |
| Titanium dioxide | 0.3 |
| Colorant | 5 |

This type of dragee can be taken 1 to 3 times per day.

Example 1e

Dragee Formulation

|  | mg/dragee |
|---|---|
| Active ingredients |  |
| *Lactobacillus paracasei* ST11 | $10^9$ cfu |
| *Lactobacillus johnsonii* | $10^9$ cfu |
| Dragee core excipient |  |
| Microcrystalline cellulose | 70 |
| Encompress ™ | 60 |
| Magnesium stearate | 3 |
| Anhydrous colloidal silica | 1 |
| Coating agent |  |
| Shellac | 5 |
| Talc | 61 |
| Sucrose | 250 |
| Polyvinylidone | 6 |
| Titanium dioxide | 0.3 |
| Colorant | 5 |

This type of dragee can be taken 1 to 3 times per day.

Examples of Compositions for Topical Application

Example 1f

Face Lotion

|  | (% by weight) |
|---|---|
| *Lactobacillus paracasei* ST11 powder | 5.00 |
| *Lactobacillus johnsonii* powder | 5.00 |
| Antioxidant | 0.05 |
| Isopropanol | 40.0 |
| Preservative | 0.30 |
| Water | qs 100% |

Example 1g

Face Care Gel

|  | (% by weight) |
|---|---|
| *Lactobacillus paracasei* ST11 powder | 5.00 |
| Hydroxypropylcellulose (Klucel H ® sold by the company Hercules) | 1.00 |
| Vitamin E | 2.50 |
| Isopropanol | 40.00 |
| Preservative | 0.30 |
| Water | qs 100% |

Example 1h

Face Care Milk

|  | (% by weight) |
|---|---|
| *Lactobacillus paracasei* ST11 powder | 5.00 |
| Glyceryl stearate | 1.00 |
| Cetylstearyl alcohol/ethoxylated cetylstearyl alcohol with 3 mol of EO (Sinnovax AO ® sold by the company Henkel) | 3.00 |
| Cetyl alcohol | 1.00 |
| Dimethicone (DC 200 Fluid ® sold by the company Dow Corning) | 1.00 |
| Liquid petrolatum | 6.00 |
| Isopropyl myristate (Estol IPM 1514 ® sold by the company Uniqema) | 3.00 |
| Glycerol | 20.00 |
| Preservative | 0.30 |
| Water | qs 100% |

Example 1i

Face Care Cream

|  | (% by weight) |
|---|---|
| *Lactobacillus paracasei* ST11 powder | 5.00 |
| Glycerol | 2.0% |
| *Vitreoscilla filiformis* extract | 3.0% |
| BHT | 0.05% |
| Methyl POB | 0.1% |
| Propyl POB | 0.05% |
| Water | qs 100% |

Example 1j

Face Care Gel

|  | (% by weight) |
| --- | --- |
| *Lactobacillus paracasei* ST11 powder | 5.00 |
| *Vitreoscilla filiformis* extract | 3.00 |
| Antioxidant | 0.05 |
| Vitamin C | 2.50 |
| Antioxidant | 0.05 |
| Isopropanol | 40.00 |
| Preservative | 0.30 |
| Water | qs 100.00% |

Example 2

An intestinal cell line CaCO-2 is cultured on 10.5 mm inserts (Becton Dickinson) at a rate of $2 \times 10^5$ cells/well. These inserts are then placed in culture in a 12-well plate (Nunc). The cells are then cultured for 21 days at 37° C. in 10% $CO_2$ and in DMEM supplemented with 10% FCS and 0.1% of penicillin/streptomycin (10 000 IU/ml, Gibco BRL).

Human peripheral blood mononuclear cells (leukocytes) are purified from blood bag buffy coats by centrifugation through a Ficoll-Hypaque 1077 column (Pharmacia) and are then resuspended in complete RPMI medium supplemented with human AB serum (Gibco BRL). The leukocytes ($2 \times 10^6$ cells/ml) are then added to the basolateral compartment of the trans-well cultures when the latter exhibit a confluent layer of CaCO-2 cells, which have been washed beforehand with their medium.

The cocultures thus established are stimulated by addition of $1 \times 10^7$ cfu/ml of probiotics to the apical surface of the monolayer of epithelial cells (CaCO-2). The system is then incubated for 16 h at 37° C./5% $CO_2$.

In order to prevent bacterial growth, 150 µg/ml of gentamicin are added to the medium after 4 h of incubation (FIG. 1).

At the end of incubation (16 h), the medium located in the basolateral compartment is withdrawn for testing.

A first analytical series consists in analysing the presence of markers of inflammation or immunoregulation (IL-8, TGF-β).

FIG. 1 illustrates the measure of the pro-inflammatory marker IL-8 produced in the media of the cocultures stimulated with the probiotic *Lactobacillus paracasei*.

There is no significant increase in IL-8 observed in the medium stimulated by *Lactobacillus paracasei* ST 11, relative to the control, a medium without stimulation by probiotics.

These results confirm the non-pro-inflammatory nature of the chosen probiotic. High levels of expression of TGF-β, moreover, were detected in this system.

The invention claimed is:

1. A cosmetic method for treating a non allergic irritant contact dermatitis of an individual in need thereof, the method comprising:
    administering to said individual an active agent comprising an effective amount of at least one:
    probiotic microorganism selected from the genus *Lactobacillus* sp.,
    a fraction of a probiotic microorganism selected from the genus *Lactobacillus* sp., and
    a metabolite of a probiotic microorganism selected from the *Lactobacillus* sp.

2. The method according to claim 1, wherein the non allergic irritant contact dermatitis is induced by at least one condition selected from the action of: chemical products, compounds capable of provoking a non allergic irritant contact dermatitis, temperature, climate, atmospheric pollution, and friction.

3. The method according to claim 2, wherein said probiotic microorganism is intended for preventing and/or reducing the irritant effect of a cosmetic or dermatological composition comprising one or more compounds capable of provoking a non allergic irritant contact dermatitis.

4. The method according to claim 1, wherein the microorganism is selected from the group consisting of *Lactobacillus johnsonii, Lactobacillus reuteri, Lactobacillus rhamnosus, Lactobacillus paracasei, Lactobacillus casei,* and mixtures thereof.

5. The method according to claim 1, wherein the microorganism is selected from the group consisting of *Lactobacillus johnsonii,* and *Lactobacillus paracasei,* deposited respectively under the following designations: CNCM I-1225, and CNCM I-2116.

6. The method according to claim 1, wherein the microorganism is *Lactobacillus paracasei*.

7. The method according to claim 1, wherein the microorganism is *Lactobacillus paracasei* CNCM I-2116.

8. The method according to claim 1, wherein said microorganism is present in a proportion of 0.0001 to 20% by weight relative to a total weight of a composition comprising said microorganism.

9. The method according to claim 1, wherein said microorganism is administered topically or orally.

10. A cosmetic treatment method for treating non allergic irritant contact dermatitis of an individual in need thereof, the method comprising administering to the individual an effective amount of at least one microorganism belonging to the species *Lactobacillus paracasei,* a fraction of a microorganism belonging to the species *Lactobacillus paracasei,* and a metabolite of a microorganism belonging to the species *Lactobacillus paracasei.*

* * * * *